United States Patent [19]

Moreno et al.

[11] Patent Number: 4,753,796

[45] Date of Patent: Jun. 28, 1988

[54] PROCESS FOR OBTAINING PROTEIN-POLYSACCHARIDE COMPLEXES INVOLVING PRECIPITATION WITH QUATERNARY AMMONIUM SALTS

[75] Inventors: Carlos Moreno, London; Mark R. Lifely, Bromley, both of England

[73] Assignee: Burroughs Wellcome Co., Research Triangle Park, N.C.

[21] Appl. No.: 883,470

[22] Filed: Jul. 11, 1986

Related U.S. Application Data

[63] Continuation of Ser. No. 554,055, Nov. 21, 1983, abandoned.

[30] Foreign Application Priority Data

Nov. 23, 1982 [GB] United Kingdom ............... 8233317
Jun. 22, 1983 [GB] United Kingdom ............... 8316951
Jun. 22, 1983 [GB] United Kingdom ............... 8316950

[51] Int. Cl.$^4$ .................... A61K 39/02; A07K 3/02; A07K 3/12; A07K 3/24
[52] U.S. Cl. .................... 424/92; 530/419; 530/806; 530/825; 536/127
[58] Field of Search ............... 424/88, 92, 177, 180; 260/112 R; 536/124, 127; 530/419, 806, 825

[56] References Cited

U.S. PATENT DOCUMENTS

| | | | |
|---|---|---|---|
| 3,983,008 | 9/1976 | Shinozaki et al. | 260/112 R |
| 4,123,520 | 10/1978 | Hagopian et al. | 424/92 |
| 4,384,113 | 5/1983 | Daly | 536/121 |
| 4,451,446 | 5/1984 | Vandevelde et al. | 260/112 R |
| 4,490,525 | 12/1984 | Hagatou et al. | 536/55.1 |

FOREIGN PATENT DOCUMENTS

0145359 6/1985 European Pat. Off. ............... 92/

OTHER PUBLICATIONS

Zollinger, W. D., et al. "Complex of Meningococcal Group B Polysaccharide and Type 2 Outer Membrane Protein Immunogene in Men", *J. Clin. Inv.*, vol. 63, May '79, pp. 836-848.

Barrett, James T. (ed.) Textbook of Immunology, 2nd ed. (1974), C. V. Mosby Co., pp. 52-54 and 244.

Beuvery, et al., "Preparation and Physiochem. & Immunol. Char. of Poly.-Outer Membrane Protein Complexes of *N. Meningitidis*", Infection & Imm., Apr. '83, vol. 40, No. 1, pp. 369-380.

Ezepchuk et al., "A Study of the Protein-Poly, Complex of *N. Memingitidis* Serogroup A", Immunochemistry, vol. 13, pp. 759-764, (1976).

Anderson et al.; "A Polysaccharide Protein Complex from *Haemophilus Influenzae* Type b"; *J. Infectious Diseases*, vol. 144, No. 6, Dec. 1981, pp. 509-520.

Frasch et al.; "Protection Against Group B *Neisseria Meningitidis* Disease: Preparation of Soluble Protein and Protein-Polysaccharide Immunogens"; *Infection and Immunity*, vol. 37, No. 1, Jul. 1982, pp. 271-280.

American Heritage Dictionary, 2nd ed., Houghton Mifflin Co., Boston, Ma.; (1982); p. 117.

Zollinger et al, Chem Abs, 91, 37312h (1979).

Zollinger et al, Infection and Immunity, 6, 835-851 (1972).

Zollinger et al, Chem Abs, 96, 179171p (1982).

Ezepchuck, Chem Abs, 86, 53731w (1977).

Richou et al, Chem Abs, 72, 11053g (1970).

*Primary Examiner*—Elizabeth Weimar
*Attorney, Agent, or Firm*—Donald Brown

[57] ABSTRACT

The invention provides a process for the insulation of an antigenic composition substantially free from cells and lipopolysaccharide, the said composition comprising a complex having a polysaccharide constituent and a protein constituent, wherein the polysaccharide constituent comprises capsular polysaccharide specific to serogroup B of *N. meningitidis*, and the protein constituent comprises *N. meningitidis* outer-membrane protein selected from the class consisting of those proteins specific to serotype 6, those proteins specific to serotype 2 and having a single dominant component having a molecular weight of 42,000±3,000, and immunological equivalents of such proteins. Preferably the composition also comprises a pharmacologically acceptable metal either as an adjuvant in admixture with the polysaccharide-protein complex, or in complex therewith to provide a triple metal-polysaccharide-protein complex. The composition is useful for the prophylaxis or treatment of bacterial disease in mammals such as man.

17 Claims, 5 Drawing Sheets

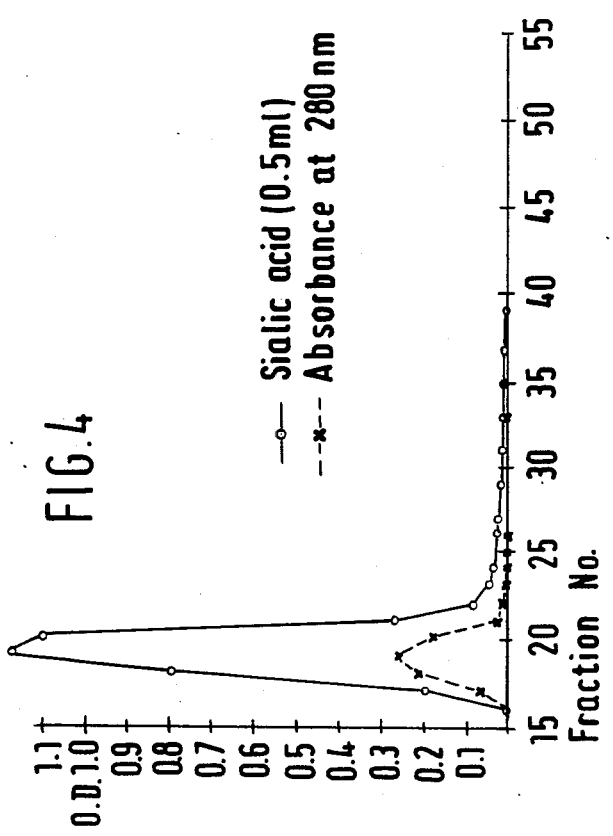
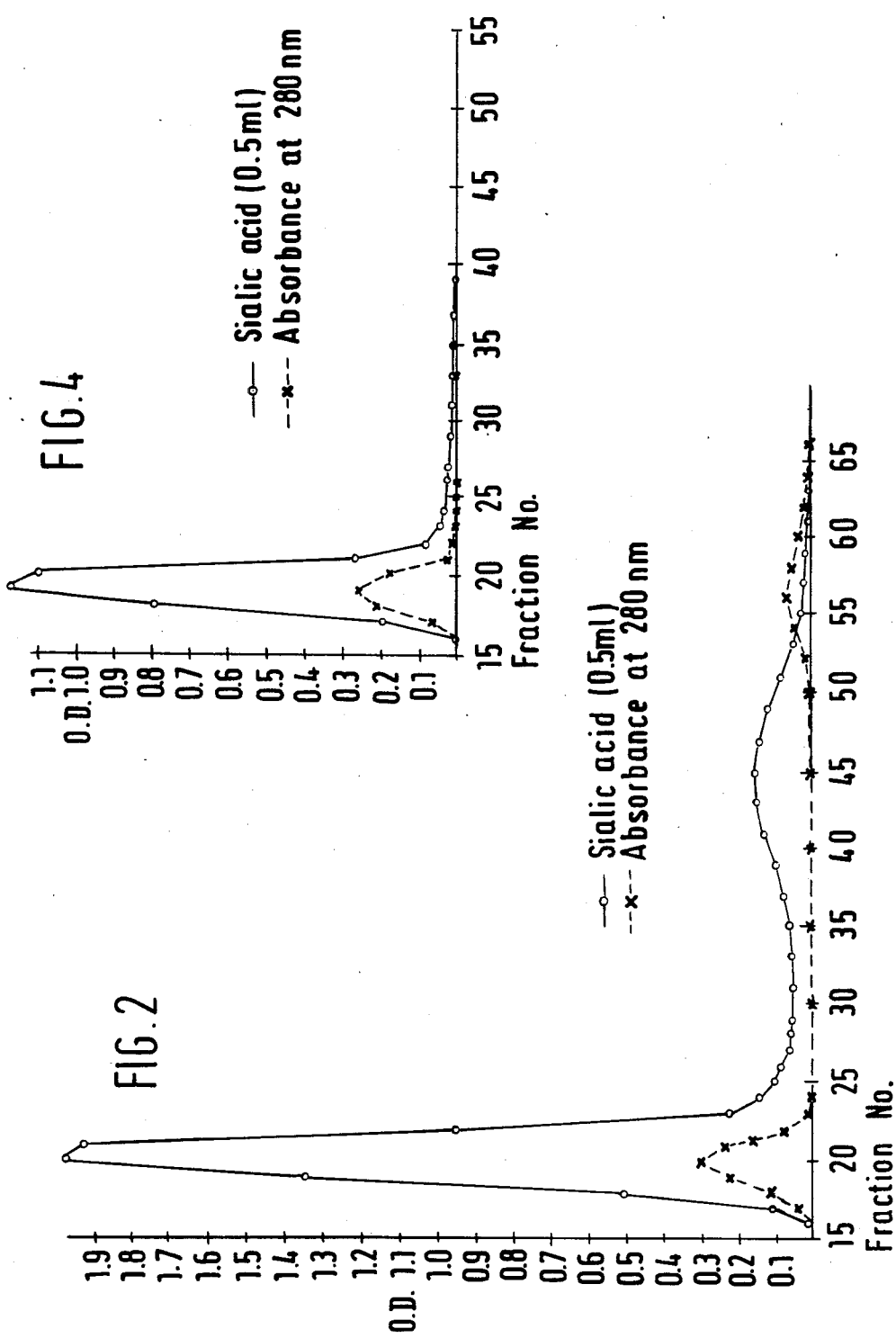

PROCESS FOR OBTAINING PROTEIN-POLYSACCHARIDE COMPLEXES INVOLVING PRECIPITATION WITH QUATERNARY AMMONIUM SALTS

This application is a continuation of application Ser. No. 554,055, filed 11/21/83, now abandoned.

The present invention relates to novel antigenic compositions comprising polysaccharide-protein complexes suitable for use in vaccines to provide protection against bacterial infections.

Certain bacteria, in addition to possessing an outer membrane structure which forms the boundary of cell envelope, also have an additional layer outside the membrane known as the capsule. An example of a gram negative bacterium with both of these features, is *Neisseria meningitidis* (*N. meningitidis*). The outer membrane of the cell envelope, contains a number of substances, including lipopolysaccharides, pili (surface protrusions), major (high molecular weight) proteins, minor (low molecular weight) proteins, lipids, and lipoproteins. Of these, the first three have been identified as principal antigens. Another important class of antigens comprises the constituents of the capsule, known as capsular polysaccharides. Capsular polysaccharides and outer-membrane proteins are believed to exist as a non-covalent complex on the exterior of the bacterium. During growth, such bacteria continuously shed capsular polysaccharides and outer-membrane proteins, in their free and complexed forms. The polysaccharides, in both forms, can be precipitated from the culture by addition of a suitable electrolyte, which also precipitates most negatively charged polymers which are present.

The serology of *N. meningitidis* enables the associated capsular polysaccharide and outer-membrane proteins to be classified according to a recognised nomenclature. There are nine recognised serogroups A, B, C, L, X, Y, Z W135 and 29E, further characterised into serotypes numbered 1-15 (see for example L. Weinstein and B. N. Fields (Eds), Seminars in Infectious Disease, Stratton Intercontinental Medical Book Corp, 1979: Chapter 10; C. E. Frasch, Noncapsular Surface Antigens of *N. meningitidis*, pp. 308-310). Different strains within a group may possess the same serotype protein, and a number of ungroupable strains have also been discovered. The capsular polysaccharides are specific to particular serogroups (group specific polysaccharides) and the major outer membrane proteins are specific to particular serotypes (type specific proteins). However, the determinants of serotypes 4, 5 and 8 are lipopolysaccharides rather than outer-membrane proteins. Thus, the capsular polysaccharides may be referred to, merely by their serogroup specicifity (eg. Group B polysaccharide) and the outer membrane proteins by their serotype specificity, (e.g. type 2 protein). This convention is generally recognised, for example, as referred to by: C. E. Frasch supra, C-M. Tsai et al in Journal of Bacteriology Vol. 146 (1981) pp. 69-78, C. E. Frasch et al in Journal of Bacteriology, Vol 127 (1976) 973-981, N. A. Vendros in T. Bergan and J. R. Norris (Eds), Methods in Microbiology, Vol 10, Academic Press, London: Chapter XI, serology of the Meningococcus, or one of the following references: C. E. Frasch and S. S. Chapman, Infection and Immunity, Vol 6 (1972) pp. 674-681; J. T. Poolman, C. T. P. Hopman and H. C. Zanen, FEMS Microbiology Letters, Vol 3 (1982) pp. 339-348. For convenience, meningococcal capsular polysaccharides (MPS) of a particular serotype, say A or C, will be referred to by the abbreviations MPS(A), MPS(C) etc, and meningococcal outer-membrane proteins of a particular serotype say 2 or 6, will be referred to by the abbreviation T(2), T(6) etc.

The *Escherichia coli* (*E. coli*) strain conventionally designated K1, contains a capsular polysaccharide known as colominic acid. This is substantially identical in structure to MPS(B).

*N. meningitidis* normally inhabits the human nasopharynx and can cause the serious and often fatal disease, cerebrospinal meningitis to which infants are particularly vulnerable. *E. coli* K1 is also responsible for some cases of meningitis in the new-born. Previous attempts to identify and isolate meningococcal antigens, have concentrated on capsular polysaccharides and the principal outer-membrane antigens referred to above, namely lipopolysaccharides, pili and major proteins. The free capsular polysaccharides, MPS(A) and MPS(C) are reasonably successful in conferring immunity against meningococcal strains belonging to serogroups A and C respectively. Serogroup B has recently been identified with increasing infantile meningococcal infection and the lack of a vaccine effective against infection by group B meningococcal strains has created a growing demand for such a vaccine from international health authorities, eg the World Health Organisation. Some immunity to Group B strains may result from vaccination with MPS(A) or MPS(C) vaccines, but the protection provided is generally not sufficient in infants, and vaccines based on MPS(B) do not confer viable immunity against infection by group B strains. Previously proposed vaccines based on (MPS)(B) suffer from the additional disadvantage that capsular polysaccharides, including MPS(B), tend to be unstable in that they are prone to intro-molecular esterification between residues (see R. Lifely, et al Carbohydrate Research, Vol 94 (1981) 193-203). Some workers have avoided free capsular polysaccharides and have isolated complexes which include capsular polysaccharides and other outer-membrane antigens. W. D. Zollinger et al in Infection and Immunity, Vol 6 (1972) pp 835-851, describes the isolation of cell wall complexes from *N. meningitidis* strains of serogroup B, serotypes 2, 3, 6 and 9 and serogroup C, serotypes 1, 2, 4, 5 and 9. These complexes each had four components: polysaccharide (4-10%); protein (45-65%); lipopolysaccharide (10-25%) and lipid (15-30%). The complexes were immunogenic in rabbits, but are unsuitable for use in vaccines because of the high toxicity of the lipopolysaccharide component. A complex of MPS(B) and T(2) specific protein was obtained in order to test its immunogenicity (see W. D. Zollinger et al in Journal of Clinical Investigation, Vol 63 (1979) pp 836-848), but such MPS(B)/T(2) complexes have previously been found to have a tendency to spontaneously dissociate, which makes them unsuitable for use in vaccines. Crude non-covalent complexes of MPS(B) with T(2) and with the varients T(2a) and T(2b) (notation according to J T Poolman et al supra) have been isolated by E C Beuvery et al (presentation at 5 ieme Conference Internationale sur la Meningite Cerebrospinale, Marseille, France, 15-17 Mar. 1983).

We have now discovered a novel and advantageous class of antigenic polysaccharide-protein complexes which may be employed in vaccines for protection against infection by meningococcal organisms, especially those of serogroups B, as well as by *E. coli* K1 organisms.

Thus, in one aspect, the present invention provides an antigenic composition substantially free from cells and lipopolysaccharide, the said composition comprising a complex having a polysaccharide constituent and a protein constituent, wherein the polysaccharide constituent comprises capsular polysaccharide specific to serogroup B of *N. meningitidis*, and the protein constituent comprises *N. menigitidis* outer-membrane protein selected from the class consisting of those proteins specific to serotype 6, those proteins specific to serotype 2 and having a single dominant component having a molecular weight of 42,000±3,000, and immunological equivalents of such proteins.

The antigenic composition according to the present invention, as defined above, is substantially free from lipopolysaccharide in that is contains a weight percentage of lipopolysaccharide insufficient to produce significant toxic effects when a given amount of the composition is administered to the human or animal body. For normal administration doses of the composition, the weight percentage will be generally 1% or less. The lipopolysaccharide may be present in the free form or associated with another constituent of the composition, for example the polysaccharide protein complex.

We have found that the immunogenic properties of the above-described compositions according to the invention may be improved by including therein a pharmacologically acceptable metal ingredient, e.g. in the form of a metal ion derived for example from an appropriate metal compound. The above-mentioned metal component may be present in the compositions in the form of a triple complex of the metal, the polysaccharide and the protein, as judged by the observation that when experimental animals are immunised with compositions containing the triple complex, antibody levels with respect to both serogroup-and serotype-specific antigens are increased, as compared with antibody levels achieved by immunisation with only the polysaccharide-protein complexes. This complexing is in contrast to the well-known adjuvant effect which would be expected to enhance antibody level only with respect to serogroup-specific antigens. We have also obtained an indication of complexing of metals with B2 and B6 complexes by NMR and electrochemical measurements relating to an aluminium-colominic acid model, and by counter immuno-electrophoresis measurements of MPS(B) concentrations in solution as a function of time, with and without the presence of aluminium.

Thus the present invention includes an antigenic composition as defined above in accordance with the present invention, the said composition further comprising a pharmacologically acceptable metal ingredient. Preferably, the metal ingredient is present in the form of a further consituent of the complex, the said complex thus comprising a polysaccharide constituent as hereinbefore defined, a protein constituent as hereinbefore defined and a further constituent comprising a pharmacologically acceptable metal. Such a complex of a metal, protein and polysaccharide, as defined, is hereinafter termed a metal triple complex.

Alternatively, the pharmacologically acceptable metal ingredient may be present in the compositions according to the invention simply in admixture with the said protein-polysaccharide complex, i.e. not in the form of the metal triple complex described above. In this case, the metal ingredient is providing an adjuvant effect with regard to the immunogenic effect of the protein-polysaccharide complex.

For convenience, throughout this specification, the following definitions apply. Unless the context requires otherwise, any reference herein to a composition means an antigenic composition according to the invention, and containing a polysaccharide-protein complex as defined above and includes those compositions containing a pharmacologically acceptable metal (whether or not in the form of a metal triple complex as hereinbefore defined). A protein-polysaccharide complex wherein the polysaccharide constituent comprises capsular polysaccharide specific to serogroup B, and the protein constituent comprises outer-membrane protein specific to serotype 6 (or immunological equivalents of such protein) is referred to herein as a B6 complex. A protein-polysaccharide complex wherein the polysaccharide constituent comprises capsular polysaccharide specific to serogroup B, and the protein constituent comprises outer-membrane protein specific to serotype 2 and having a single dominant component having a molecular weight of 42,000±3,000 (or immunological equivalents of such protein) is referred to herein as a B2 complex. The corresponding metal triple complexes are termed metal-B6 and metal-B2 complexes respectively. The general term, a complex according to the invention, means, a B2, B6, metal-B2 or metal-B6 complex as defined.

The pharmacologically acceptable metal ingredient referred to above, either as an adjuvant or as a constituent of metal triple complexes must be pharmacologically acceptable in the sense that its identity, chemical form (e.g. ion) and amount must be tolerated by the recipient for as long as it remains in the body thereof. Such a metal ingredient may for example be selected from pharmacologically acceptable metals in groups IIA, IB, IIB and IIIB of the periodic table, as well as the transition metals, especially those of group VIII. Preferred metals include aluminum, zinc, iron, nickel and calcium. The metals are preferably provided in ionic form, for example the $Al^{3+}$, $Zn^{2+}$, $Fe^{3+}$, $Ni^{2+}$ and $Ca^{2+}$ ions. An especially preferred metal is aluminum, particularly in the form of the $Al^{3+}$ ion.

Outer-membrane proteins derived from mutants of *N. meningitidis* strains may be regarded as "immunologically equivalent" to those isolated from serotype 2 or 6 meningococci when the gel electrophoresis characteristic patterns of the outer-membrane proteins of such mutants do not necessitate classification of the mutant organisms in another recognised serotype, and their immunological properties are not substantially altered. Such mutants may be found in nature as has been found with mutants of serotype 2 (per Poolman et al supra) or may be produced by techniques known to those skilled in the art.

In experiments in mice, B2 and B6 complexes have been found to provide significant immunological protection against challenge by group B meningococci and *E. coli* K1 strain. Furthermore, these complexes confer immune system memory, so that secondary immunisation at a later date, using a smaller amount of complex than that used for the primary immunisation, confers a significant increase in protection. This contrasts with free capsular polysaccharide antigens (including MPS(B)) known in the art, which have previously been found not to confer such memory when administered by successive injections of the purified form. Complexes according to the invention also appear to be less susceptible to the instability and dissociation referred to above in relation to free capsular polysaccharides, especially MPS(B), and previously isolated MPS(B)/T(2) complexes and thus they are more suited to formulation of vaccines. In addition, B2 and B6 complexes are unexpectedly successful in conferring immunity against infection by group B meningococci.

The complexes according to the invention comprise essentially only two or three constituents (namely capsular polysaccharide, outer-membrane protein and optionally, a pharmacolgically acceptable metal) as opposed to four in the case of the complexes described by Zollinger et al in Infection and Immunity supra. In particular they do not include substantial amounts of toxic lipopolysaccharide as do the four-component complexes. The complexes generally have a molecular weight of at least $2 \times 10^7$ when determined by chromatography on Sepharose CL-2B (Trade Mark). The ratio of polysaccharide to protein in B6 complexes is generally between 0.2:1 w/w and 5:1 w/w, typically about 1:1 w/w. In the case of B2 complexes, the ratio is generally between 0.2:1 w/w and 10:1 w/w, typically about 2.5:1 w/w. Column chromatography of the B2 and B6 complexes yields a single peak, demonstrating that the two components indeed exist as a complex and not as a mere mixture. However, the components may be dissociated by treatment with a suitable detergent such as sodium dodecyl sulphate, eg. in order to perform characterisation tests on them separately, as described below. Such dissociation may be verified by column chromatography which consequently yields two separate peaks. This is evidence that the components of the complexes are non-covalently bonded, in particular hydrophobically (ie. lipophilically) bonded.

Gel electrophoresis, particularly sodium dodecyl sulphate-polyacrylamide gel electrophoresis (SDS-PAGE) of complexes according to the invention provides patterns characteristic of their protein components. We have determined this serotype specificity using the SDS-PAGE procedure described by U. K. Laemmli in Nature (London) Vol 227 (1970) pp. 680–685. The serotype specificity of the proteins in a complex according to the invention may for example be verified by comparison of its pattern with those given in the above literature references concerned with meningococcal serology and its experimental determination eg. C. E. Frasch et al in Journal of Bacteriology supra. We have confirmed the serotype specificity of proteins in B6 complexes as type 6 simply by identification in their electrophoresis patterns (using the Laemmli procedure) of two major bands at the same positions as those obtained using previously authenticated substantially pure serotype 6 protein as a marker. Alternatively, if standard MW markers are used, the serotype specificity of the protein components of B6 complexes may be confirmed as type 6 if there are major bands at about 43–44,000 and 38–40,000 when using the Laemmli procedure after boiling the sample for 3 minutes in SDS at 95° C. In the case of B2 complexes, their serotype specificity has been confirmed as type 2 by electrophoresis (again using the Laemmli procedure). B2 complexes yield only one major band which occurs at the same position as one of those appearing in the patterns of authenticated substantially pure serotype 2 protein. This band corresponds to a dominant protein component at a molecular weight of about 42,000 when using the Laemmli procedure after boiling the sample for 3 minutes in SDS at 95° C.

The serogroup specicifity of the capsular polysaccharide component of a complex according to the invention may be verified by any appropriate method of compositional analysis known to those skilled in the art. For example meningococcal serogroup B capsular polysaccharides are known to comprise sialic acid, which may be determined by colorimetric methods. The polysaccharide component may also be determined by nuclear magnetic resonance, or immunologically with specific antisera.

The antigenic compositions according to the present invention may optionally include one or more other antigenic components e.g. free MPS(A) and MPS(C) as well as one or more other complexes of meningococcal capsular polysaccharide and outer-membrane protein such as MPS(B)/T(7), MPS(C)/T(2) or MPS(A)/T(2) in order to provide a broader spectrum of immunity. The antigenic compositions may simultaneously contain more than one complex selected from 2, B6, metal-B2 and metal-B6.

In another aspect, the present invention also provides a process for the isolation of a complex of a bacterial capsular polysaccharide and a bacterial outer-membrane protein, the process comprising the steps:

(i) culturing in a medium, a bacterium which possesses an outer-membrane and capsule and obtaining an aqueous phase which includes a complex of a bacterial capsular polysaccharide and a bacterial outer-membrane protein;

(ii) admixing the aqueous phase obtained in step (i) with a quaternary ammonium salt, to effect precipitation of a precipitate containing the said complex;

(iii) admixing the precipitate obtained in step (ii) with a water-soluble salt of calcium or magnesium in an aqueous medium to form an aqueous solution which includes said complex as a solute;

(iv) admixing the aqueous solution obtained in step (iii) with a lower alkanol, to effect precipitation of a precipitate containing the said complex; and (v) separating the complex from any other components present in the precipitate resulting from step (iv).

The process of the invention described above may be used to isolate any B2 or B6 complex (eg. those described above in accordance with the present invention), other protein/polysaccharide complexes from *N. meningitidis*, (eg MPS(A) or MPS(C) complexed with T(2) or T(6) or MPS(B) complexed with T(7) and protein/polysaccharide complexes from any other bacteria possessing both a capsular polysaccharide and an outer-membrane protein. Thus, the appropriate bacterium is cultured in step (i) of the process. The process provides the desired complex in a relatively pure form, substantially free, for example, from complexes other than that it is intended to isolate, lipopolysaccharides, lipids and other impurities, and enables one to obtain the complexes directly.

Prior-art processes generally suffer the disadvantage of dissociating the protein and polysaccharide components necessitating their recombination, although the crude complexes of Beuvery et al supra were isolated intact.

In performing the process of the present invention, the aqeuous phase is desirably obtained before the culture has reached a stationary phase, in order to minimise the isolation of lipopolysaccharide. It is also advantageous to remove the bacterial cells and cell debris from the aqueous phase, for example by centrifugation, before performing the precipitation of step (ii), although such removal may be effected at any appropriate stage of the process. In step (ii), the quaternary ammonium salt is desirably cetyl-trimethylammonium bromide, ie Cetavlon (Trade Mark) or cetylpyridinium chloride. Such salts are used to form an insoluble complex salt with the free capsular polysaccharide which is present, and thus they are readily eliminated in steps (iii) and (iv). This facile elimination contrasts with prior-art processes for isolation of non-complex antigens, wherein a detergent such as sodium dodecyl sulphate is used for separating the antigens from other bacterial fragments, and is subsequently difficult to eliminate (although the presence of detergents in vaccines in undesirable). As well as the desired complex, the precipitate formed in this step of the process, also contains everything else negatively charged which is present in the aqueous phase, ie proteins (including those from the outer-membrane), lipopolysaccharide and partially degraded nucleic acids. When cetavlon is used, the step (ii) precipitation is desirably performed at a temperature in the range from 12° to 25° C., optimally at or about 18° C. When the salt is cetylpyridinium chloride, the precipitation may be performed at a temperature in the range 0°–10° C., optimally at or about 4° C. In either case, the salt is perferably present at around 1% w/v.

The water-soluble salt referred to in step (iii) is preferably calcium chloride. As well as the complex, the solution in step (iii) also contains, as a solute, the other components present in the precipitate formed in step (ii), but not the capsular polysaccharide complex salt, which is thus eliminated.

In performing the above process, the alkanol is used in step (iv) in an amount and at a concentration so that there occurs substantially no dissociation of a polysaccharide/protein complex. Preferably, the alkanol is used to provide a concentration in the range of 50–95% v/v when in admixture with the aqueous solution. A particularly prefered concentration is about 75%. As used herein, the term "lower alkanol" denotes an alkanol containing 1 to 4 carbon atoms, for example ethanol or methanol. In addition to the complex, the precipitate formed in step (iv) also contains some low molecular weight impurities such as outer-membrane protein, low molecular weight nucleic acid fragments and a little lipopolysaccharide. These impurities are substantially eliminated in the separation in step (v), which is preferably performed by gel filtration, eg using Sepharose CL-2B or any other system having similar properties.

Further purification, if required, may be carried out on the product of step (v), as described hereinafter, in order to minimise the presence of contaminating materials such as degraded nucleic acids and uncomplexed polysaccharides and proteins.

Where the process is used to prepare a B2 or B6 complex, it may include a further step of bringing the complex product into association with a pharmacologically acceptable metal, thereby to form a metal triple complex as hereinbefore defined. The metal may for example be any of those indicated previously, and is generally employed as a compound thereof (eg as an ion of a metal salt). It is desirable that the metal and B2 or B6 complex are brought into association in solution. This may entail admixture of a solution of B2 or B6 complex and a solution containing the metal (eg. as a metal ion derived from a salt thereof), and optionally if desired, incubating the resulting mixture. Alternatively the two solutions may be brought into association by dialysis of one against the other. Preferably the solvent in each case is water, optionally containing one or more solubilising agents. Suitable metal salts include water soluble salts such as those derived from inorganic and organic acid anions, for example halides (ie. fluorides, chlorides, bromides and iodides) sulphites, sulphates, nitrites, nitrates, phosphates, alkanoates (eg acetates), benzoates, succinates, phthalates and oxalates.

The present invention further provides a vaccine formulation comprising a composition according to the present invention and at least one adjuvant and/or carrier therefor. In such formulations, the composition may include further antigenic components described above, such as one or more free meningococcal capsular polysaccharides. A vaccine intended to provide protection against meningococci of serogroups B and A and/or C can contain respectively a mixture of one or more complexes according to the invention, together with MPS(A) and/or MPS(C). Alternatively, such formulations may contain, if desired, complexes according to the invention, and one or more complexes of meningococcal capsular polysaccharide and outer-membrane protein such as MPS(B)/T(7), MPS(C)/T(2), or MPS(A)/T(2).

The vaccine formulations according to the present invention may be presented in a sterile form, such as is suitable for administration to humans. In these formulations, the carrier may for example be water. As well as the metal adjuvants referred to previously, such a formulation may additionally or alternatively contain one or more appropriate non-metal constituents such as lactose as an antigen stabiliser, or one or more salts, such as sodium chloride, to render the vaccine isotonic with blood. Preferably, an appropriate buffer is also included. In such vaccines, the complex according to the invention may conveniently be administered in a dosage of from 0.1 $\mu$g to 3 mg, desirably 1.0 to 300 $\mu$g, preferably about 50 $\mu$g.

The invention further provides a process for preparation of a vaccine formulation, the process comprising admixture of a composition and at least one adjuvant or carrier therefor. In the process, the vaccine may be rendered sterile, eg. by detergent-assisted filtration.

In another aspect, the invention provides a composition according to the present invention for use in the prophylaxis or treatment of a bacterial (eg meningococcal or E. coli) disease of a mammal such as man. For example, the composition may be used for the prophylaxis or treatment of cerebrospinal meningitis. In such use, the composition may be presented in any formulation described herein. The composition may be administered in one or more doses. If more than one dose is administered, it is desirable that the administration is spaced over a suitable time scale to take advantage of secondary immunisation. The composition may for example be administered as two or three doses, for example over an interval one to three weeks. Where appropriate, doses subsequent to the first, may contain amounts of the complex which are less than the amount contained in the primary dose. The composition may be administered by any convenient route such as the parenteral (e.g. sub-cutaneous, intravenous, intra-peritoneal), oral, or as may be desirable for infants, intra-nasal route. The invention also provide a method of prophylaxis or treatment of a bacterial (eg meningococcal or E. coli) disease of a mammal such as man, comprising administration of an effective amount of a composition according to the present invention to said mammal. The composition is advantageously employed in the form of a vaccine formulation according to the invention. Other aspects of the invention include complexes produced by the process of the invention, as defined above; the use of such a complex in the treatment or prophylaxis of a bacterial (eg. meningococcal or *E. coli*) disease of a mammal such as man, for example in a vaccine formulation; and a method of such treatment of prophylaxis by administration to the mammal of such a complex.

The following examples illustrate the present invention, reference being made to the accompanying drawings, in which:

FIG. 2 shows the elution profile of a typical crude B2 complex from a Sepharose CL-2B chromatographic column by monitoring absorbance of the fractions at 280 nm, and by sialic acid determination by the resorcinol-HCl colorimetric method.

FIG. 4 shows the elution profile upon Sepharose CL-2B re-chromatography of the purified typical B2 complex by monitoring absorbance of the eluent at 280 nm, and by sialic acid determination by the resorcinol-HCl colorimetric method.

EXAMPLE 1

Figure 1:
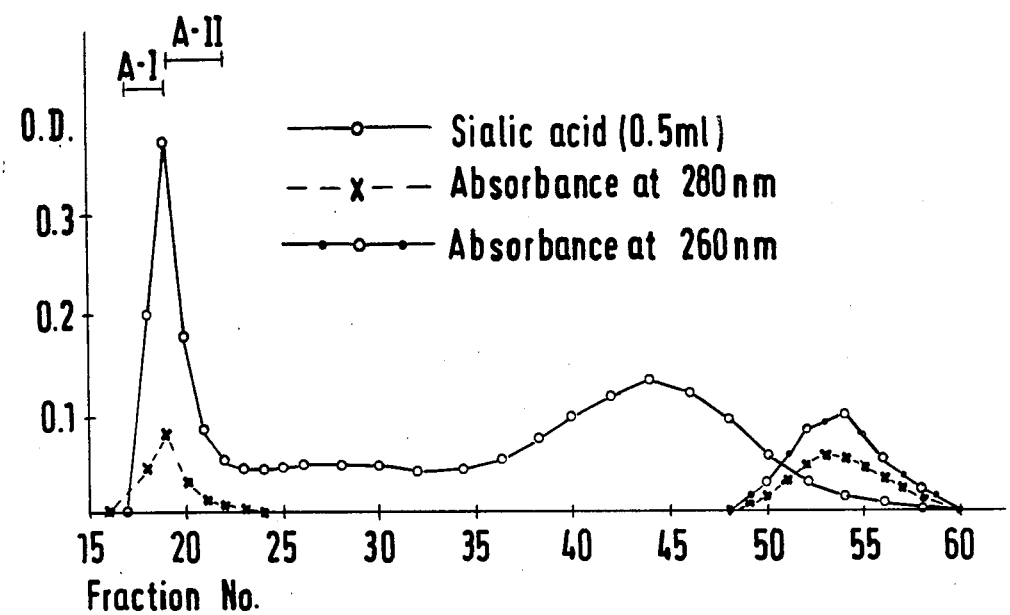
FIG. 1 shows the elution profile of a typical crude B6 complex from a Sepharose CL-2B chromatographic column by monitoring absorbance of the fractions at 260 and 280 nm, and by sialic acid determination by the resorcinol-HCl colorimetric method.
Figure 3:
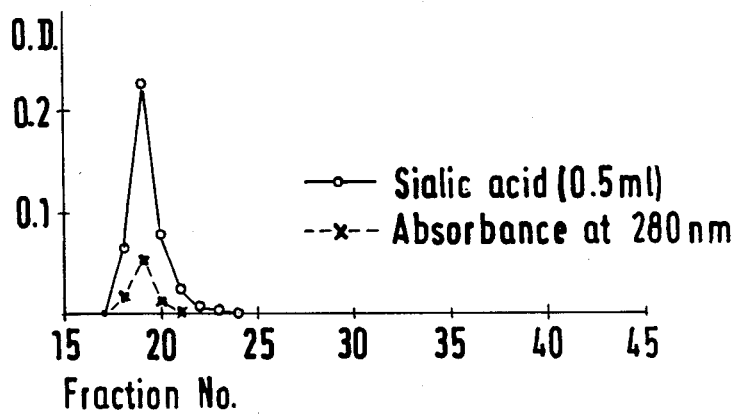
FIG. 3 shows the elution profile upon Sepharose CL-2B re-chromatography of the purified typical B6 complex by monitoring absorbance of the eluent at 280 nm, and by sialic acid determination by the resorcinol-HCl colorimetric method.
Figure 5:
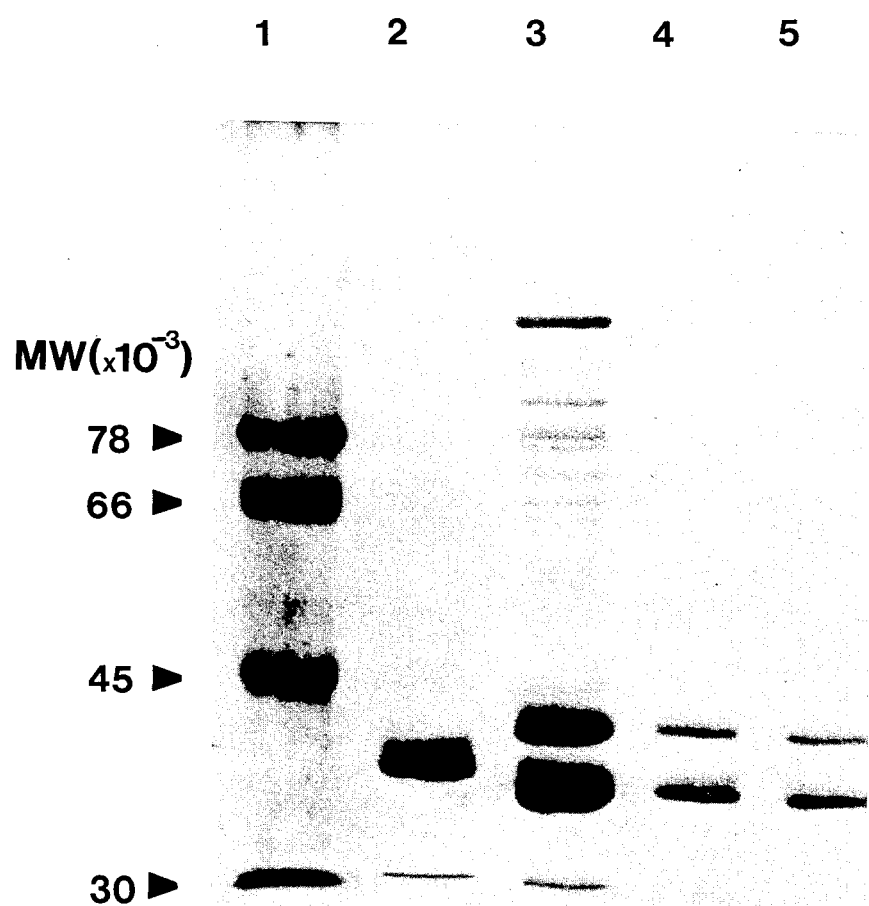
FIG. 5 shows patterns obtained from SDS-PAGE of B2 and B6 complexes, and molecular weight marker standards.

Isolation and Purification of a B6 Complex

A culture medium was prepared as an aqueous solution of the following ingredients, in the amounts stated, and the resultant solution was made up to a volume of 16 liters with added water.

|  | Per liter | per 16 liters |
|---|---|---|
| $K_2HPO_4$ | 230 mg | 3.68 g |
| L-Glutamic acid | 1.30 mg | 20.8 g |
| Cysteine HCl | 130 mg | 0.48 g |
| $NaHCO_3$ | 842 mg | 13.47 g |
| Tricine, N tris (hydroxymethyl) methyl glycine | 716 mg | 11.46 g |
| $FeSO_4 7H_2O$ | 2.8 mg | 0.045 g |
| $NH_4Cl$ | 500 mg | 8.0 g |
| $K_2SO_4$ | 48 mg | 0.77 g |
| $CaCl_2 2H_2O$ solution, 7.4 mg/100 ml | 1 ml | 16 ml |
| $MgCl_2 6H_2O$ | 107 g | 1.71 g |
| Casein Hydrolysate | 20 g | 320 g |

The pH of the solution was adjusted to pH 7.2 and two 400 ml aliquots were transferred to two, one liter conical flasks. The remainder of the solution was transferred to a 15 liter bottle. A siphon was connected to the bottle and both flasks and the bottle were autoclaved for 15 minutes at a pressure of 15 lb/sq inch. The contents of the bottle were then transferred to a 20 liter fermenter and 300 ml of sterile 50% aqueous glucose was added, to form the medium. An inoculum was prepared by adding one drop of a culture containing a serogroup B, serotype 6 strain of *N. meningitidis*, to both flasks containing 400 ml of the solution.

The flasks were incubated at 37° C., with shaking, for 12 hours, to form 800 ml of seed culture, the purity of which was checked by the Grams stain technique.

All of the seed culture was then used to inoculate the medium in the fermenter. The whole culture medium was then grown under the following experimental conditions.

| | |
|---|---|
| Temperature | constant at 37° C. |
| pH | constant at 7.2 with sterile 2NHCl and 2NNaOH |
| Stirring speed | 100-700 rpm automatically adjusted. |
| Dissolved oxygen | minimum 10% saturation. |
| Air flow | 1-5 liter per minute adjusted manually to maintain dissolved oxygen concentration. |
| Antifoam | Polypropylene glycol added manually when required. |

The culture was allowed to grow until an optical density of approximately 9.0 was reached. This O.D. might normally be expected to be achieved after about 6.5 hours.

The culture was then transferred from the fermenter and passed through a continuous flow centrifuge at a flow rate sufficient to produce a substantially clear supernatant. Following the centrifugation, to the supernatant was added, 1% by volume of 10% w/v Cetavlon in water, to produce a precipitate in suspension. The suspension was centrifuged at 2000 rpm at 4° C. The supernatant was then discarded, and the precipitate was suspended in 600 ml of water. 600 ml of 2M aqueous calcium chloride was then added and the mixture stirred for 1 hour at 4° C., then centrifuged for 20 minutes at 5000 rpm.

To the supernatant was added one drop of caprylic alcohol as an anti-foaming agent and the supernatant was de-gassed under vacuum, with stirring, for 10 minutes. The de-gassed supernatant was stood in an ice bath, and to it was added 3 volumes of absolute ethanol at 0° C. with continuous stirring. The mixture was then stood in the bath for two hours before being centrifuged at 5000 rpm for 15 minutes, at a temperature of 4° C. The supernatant was discarded and the precipitate re-suspended in 75% ethanol and centrifuged as before. The supernatant was again discarded and the precipitate dissolved in 200 ml of water and freeze dried. (It is also possible to spin-down the preciptate to form a pellet which may be stored at −20° C. or treated as below).

The dried material was dissolved at a rate of 20 mg/ml in 0.1M ammonium acetate containing 0.01% thiomersalate and centrifuged at 20,000 g for 20 minutes to remove insoluble material. (The solution may be subjected to ultrasonic agitation for 10 minutes, prior to centrifugation). The supernatant was then passed through a 5 liter column of Sepharose CL-2B equilibrated with buffer at 4° C. The column was washed through with buffer, and the effluent monitored by UV absorption at the wavelength 260 and 280 nm and resorcinol-HCl sialic acid determination. The void volume fractions exhibiting absorption at 280 nm and containing sialic acid (resorcinol-HCl determination) were pooled. Sodium deoxycholate was added up to a final concentration of 0.1% w/v buffered to within pH 8-9. (Other concentrations and pH values are also possible, eg a final concentration of 1% w/v buffered to pH 11 has been found to reduce the amount of material which adheres to the membrane). The resultant solution was immediately filtered through a Sartobran 0.22μ capsule with a 0.45μ prefilter. The filtrate was precipitated with 3 volumes of absolute ethanol (concentration after solution about 75%). After this filtration, all procedures were performed under sterile conditions. The supernatant was then discarded, and the precipitate suspended in 200 ml of cold ethanol to wash it. The suspension was then centrifuged, the supernatant discarded, and the precipitate (which comprised substantially only the B6 complex) was, again subjected to the same washing process before being redissolved in 200 ml of cold water. (Alternatively, injectable solutions may be prepared eg. with 5% lactose and 0.01M $Na_3PO_4$; pH 7.3).

EXAMPLE 2

Isolation and Purification of a B2 Complex

A B2 complex was prepared by the process of Example 1, starting from a culture containing a serogroup B, serotype 2 strain of *N. meningitidis*.

EXAMPLE 3

Isolation and Purification of a B6 Complex: Small-Scale Process

Three liters of diluted culture medium were prepared by a method analogous to that used in Example 1, using the same ingredients. A portion of about 200–500 ml of the medium was transferred to a non-baffled shaped-flask and inoculated with 1 drop of a culture containing a serogroup B, serotype 6 strain of *N. meningitidis.* The inoculum was incubated as specified in Example 1, then added to the remainder of the culture medium, which was incubated in a manner analogous to that described in Example 1, for 6.75 hours. The culture was then transferred as 6×500 ml to a centrifuge and centrifuged for 20 minutes at 7000 rpm.

To the supernatant was added 1% by volume of 10% w/v Cetavlon. The suspension was left to settle at 4° C. for 16 hours, after which, the major part of the supernatant was syphoned off, and the remainder, containing the precipitate, was centrifuged at 2000 rpm for 20 minutes at 4° C. The precipitate was resuspended in 20 ml of distilled water, 20 ml of 2M $CaCl_2$ was added, and the mixture stirred for 1 hour at 4° C., then centrifuged for 20 minutes at 5000 rpm.

The the supernatant was added absolute ethanol to a final concentration of 75% v/v, and after 1 hour, the precipitate was collected by centrifugation, washed twice with absolute ethanol, twice with acetone and dried in vacuo. The yield of precipitate was about 100 mg per liter of culture.

The crude precipitate was redissolved and part-purified by chromatography on a 500 ml column of Sepharose CL-2B, as described in Example 1. The void volume fractions containing sialic acid and material absorbing at 280 nm were pooled, precipitated by addition of ethanol to a final volume of 75% v/v, then collected by centrifugation at 15,000 g for 20 minutes at 4° C. The precipitate was washed with absolute ethanol and freeze-dried.

EXAMPLE 4

Isolation and Purification of a B2 Complex: Small Scale Process

A B2 complex was prepared by the process of example 3, starting from a culture containing a serogroup B, serotype 2 strain of *N. meningitidis.*

EXAMPLE 5

Characterisation of Complexes

The complexes formed in Examples 1–4 were identified in each case as the peak eluting in the void volume on Sepharose CL-2B (MW $20\times10^6$) at 4° C. as assayed for sialic acid by the resorcinol-HCl method and for absorbance at 260 and 280 nm in the case of B6 complexes (see FIG. 1) and at 280 nm only in the case of B2 complexes (see FIG. 2). The latter plot was obtained from a freeze-dried sample of a B2 complex having a sialic acid content of 48% and a protein content of 36.1% (ratio 1.33:1). The complexes were found not to dissociate (ie. protein and polysaccharide remain in the void volume) upon re-chromatography on Sepharose CL-2B (FIG. 3 for the complex used in FIG. 1 and FIG. 4 for the complex used in FIG. 2) at 4° C. SDS-PAGE of the complexes gave the protein component pattern characteristic of serotype 6 for the products of Examples 1 and 3 and serotype 2 for the products of Examples 2 and 4; the samples were boiled for 3 minutes in SDS at 95° C. then subjected to the procedure of Laemmli supra. 10 ug of sample per track, staining with Coomassie blue. In FIG. 5, track 1 shows molecular weight marker bands. Track 2 was obtained from a B2 complex. The pattern of track 2 shows a major band due to a dominant protein component having a molecular weight in the region of 42,000. A minor band also appears around 32,000. Track 3 was obtained from a crude precipitate including B6 complex obtained by precipitation with 1% Cetavlon and before purification. Tracks 4 and 5 were obtained from samples of freeze-dried B6 vaccine compositions obtained from isolation processes including precipitation with cetylpyridinium chloride, the tracks being from samples, respectively before and after sterile filtration. Chemical composition of the complexes was determined by colorimetric methods, for sialic acid (resorcinol-HCl), and for protein (Lowry method using a standard of bovine serum albumin). Endotoxin was determined by the rabbit pyrogenicity test and by the chick embryo toxicity test as described below in Example D.

EXAMPLE 6

Preparation of an Aluminium-B6 complex

A B6 complex, isolated by the method of Example 1 was complexed with aluminium by preparation of a solution as 0.5 ml aliquots, each containing: 10 μg B6 complex in 5% lactose; 0.01M sodium phosphate to pH 7.4, 0.001M $Al_2(SO_4)_3$.

EXAMPLE A

Immunisation of Mice with a B6 complex

Female, 8 week old $CBAT^6T^6$ mice, 5 per group, were immunised with 0.1, 1.0 and 10.0 μg doses of B6 complex (prepared according to the method of Example 2) in 0.2 ml of phosphate-buffered saline pH 7.2, injected intraperitoneally (Exp A) or subcutanteously (Exp B). Individual bleedings were taken from the mice at 7, 14 and 21 days after immunisation. The antibody level was determined as µg/ml of serum, by solid phase radioimmunoassay in plate sensitised with purified group B meningococcal polysaccharide. In this method, microtiter soft plates were pre-treated with poly L-lysine (Sigma, 100 µg per ml) and sensitised with the polysaccharide. After incubation with the complex, wells were counted and a linear correlation between the counts and $\log_2$ of the serum dilution was obtained. Extrapolated values at 1/50 dilution of serum were compared with linear correlations of a standard.

| | Antibody level: µg per ml of serum (standard error) measured after days: | | |
|---|---|---|---|
| | 7 | 14 | 21 |
| | Exp A | | |
| Dose (µg/mouse) | | | |
| 10 | 2.4(1.03) | 2.6(1.07) | 1.6(1.05) |
| 1.0 | 2.8(1.10) | 2.4(1.06) | 2.0(1.07) |
| 0.1 | 4.2(1.16) | 2.9(1.11) | 2.6(1.11) |
| — | | 1.4(1.05) | |
| | Exp B | | |
| Dose (µg/mouse) Days: | | | |
| 10 | 5.1(1.05) | 4.0(1.05) | 1.6(1.11) |
| 1.0 | 3.6(1.13) | 2.9(1.12) | 2.6(1.31) |
| 0.1 | 1.3(1.12) | 1.0(1.06) | 1.9(1.04) |
| — | | 1.4(1.05) | |

EXAMPLE B

Protection of Mice after Immunisation with B6 complex
Exp 1 (Primary Immunisation)

Intraperitoneal injections of B6 complex (prepared according to the method of Example 2) were administered to CBA[6] female mice, eight weeks old at the onset of the experiment (this designated Day 0). Controls were injected with free MPS(B) or not injected. On Day 21, the mice were intraperitoneally injected with one or other of two strains of *N. meningitidis* in combination with 10 mg of iron dextran, one of serogroup B, serotype 2 and another of serogroup B, serotype 6. Results were recorded as dead mice/total at 72 hours after challenge.

| Day 0 (Immunisation) | Day 21 (Challenge with strain of group B, type 2 (72 hours death/total) | Day 21 (Challenge with Strain of group B, type 6 (72 hours death/total) |
|---|---|---|
| 1000 ng complex | 1/8 | 1/8 |
| 100 ng complex | 5/8 | 4/8 |
| 1000 ng free MPS(B) | 8/8 | 5/8 |
| 100 ng free MPS(B) | 8/8 | 7/8 |
| Not Injected | 8/9 | 7/9 |
| RMW/KMS/DC6/04.11.83 | | |

It was found that free MPS(B) produces no detectable change in protective levels measured.

Exp 2 (Secondary Immunisation)
Four batches of the same mice were used, the first batch were given primary immunisation (with B6 complex as per Exp 1 above) on Day 0 and secondary immunisation on Day 21, the second batch were given ony the primary immunisation, the third batch were given only the secondary immunisation, and fourth batch were given no immunisation. The mice were challenged with intraperitoneal injections, as Experiment 1 with strain CN 7622 on Day 26. Again, results were recorded as dead mice/total at 72 hours after challenge.

| Day 0 (Immunisation) | Day 21 (secondary Immunisation) | Day 26 (Challenge)(72 hours death/total) |
|---|---|---|
| 100 ng complex | 1 ng complex | 1/8 |
| 100 ng complex | — | 5/8 |
| — | 1 ng complex | 10/10 |
| — | — | 7/8 |

EXAMPLE C

Protection of Mice after Immunisation with B2 Complex

CBA mice were vaccinated with B2 complex and challenged with a group B, type 6 strain (with iron-dextran) 21 days after vaccination (Exp 1) or with a group B, type 2 strain, 7 days after vaccination (Exp 2).

| | 72 hour mortality/total |
|---|---|
| Exp 1 | |
| 0.1 µg B2 complex injected i.p. | 0/5 |
| non-vaccinated control | 8/10 |
| Exp 2 | |
| Dose (µg/mouse i.p.) | |
| 10 | 0/5 |
| 1 | 1/5 |
| 0.1 | 1/5 |
| — | 5/5 |

EXAMPLE D

Results of Chick Embryo Toxicity (CET) Tests and Rabbit Pyrogenicity Tests

Both tests were performed for three batches (A, B and C) of purified B6 complex prepared according to the method of Examples 1 and 3. Batch A was divided into the leading (A1) and trailing (A2) fractions of the void volume peak from Sepharose CL-2B chromotography (see FIG. 1).

| Purified Complex Batch | CET LD50 (µg) | Rabbit Pyrogenicity Given as Rise (°C.) | | |
|---|---|---|---|---|
| | | 50 µg/Kg Complex | 0.25 µg/Kg Complex | 0.025 µg/Kg Complex |
| A1 | 8.8 | 1.27 | 1.23 | 0.7 |
| A2 | 7.1 | — | — | — |
| B | 5.8 | — | — | — |
| C | 7.1 | 2.07 | 1.15 | 0.63 |

*E. coli* lipopolysaccharide was used as CET reference, and gave an LD50 of 0.04 µg.

EXAMPLE E

Immunisation of Mice with an Aluminium-B6 Complex

The level of antibodies produced against group B and type 6 antigens respectively was measured in mice at 7, 14 and 21 days after secondary immunisation with an aluminium-B6 complex prepared by the method of Example 6. The protocol was that used for the experiments of Example A. Test and reference preparations in each case were prepared as follows:

| Preparation No. | Injection Solution |
|---|---|
| 1. | 10 µg B6 complex, 5% lactose, 0.01 M Na₃ |

-continued

| Preparation No. | Injection Solution |
|---|---|
|  | PO4 pH 7.4 (0.5 ml) i.p. |
| 2. | 5% lactose, 0.01 M Na3PO4 pH 7.4 (0.5 ml) i.p. |
| 3. | Solution of Example 6 (0.5 ml) i.p. |
| 4. | 5% lactose, 0.01 M Na3PO4 pH 7.4, 0.001 M Al2(SO4)3 (0.5 ml) i.p. |
| 5. | 10 μg B6 complex, 5% lactose, 0.01 M Na3PO4 pH 7.4, 500 #g steorolyl tyrosine (0.5 ml) i.p. |
| 6. | 5% lactose, 0.01 M Na3PO4 pH 7.4, 500 μg sterolyl tyrosine (0.5 ml) i.p. |

Figure 6:
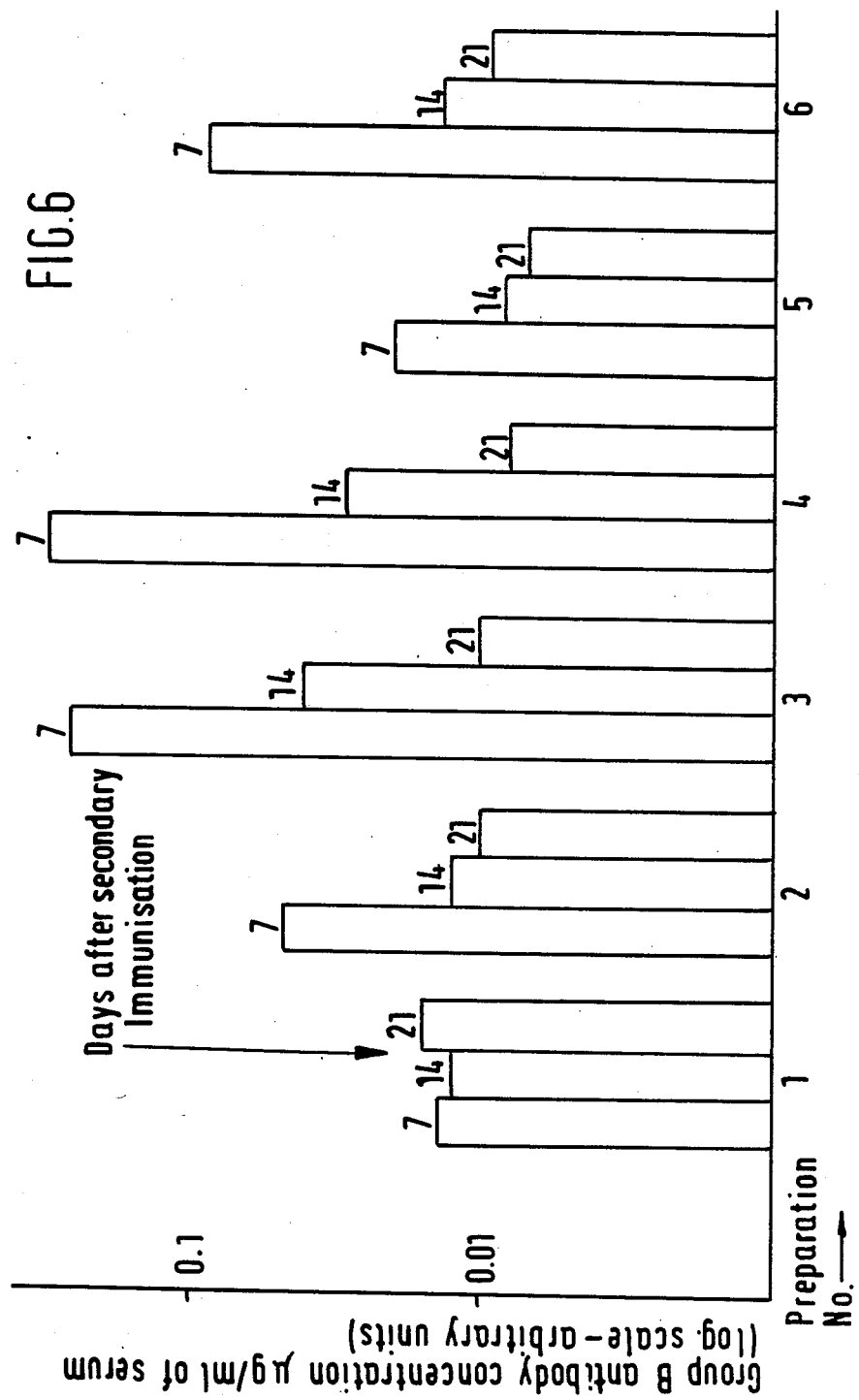
FIG. 6 shows the antibody response in mice with respect to serogroup B antigens after secondary immunisation with B6 and aluminium-B6 preparations, and with controls.
Figure 7:
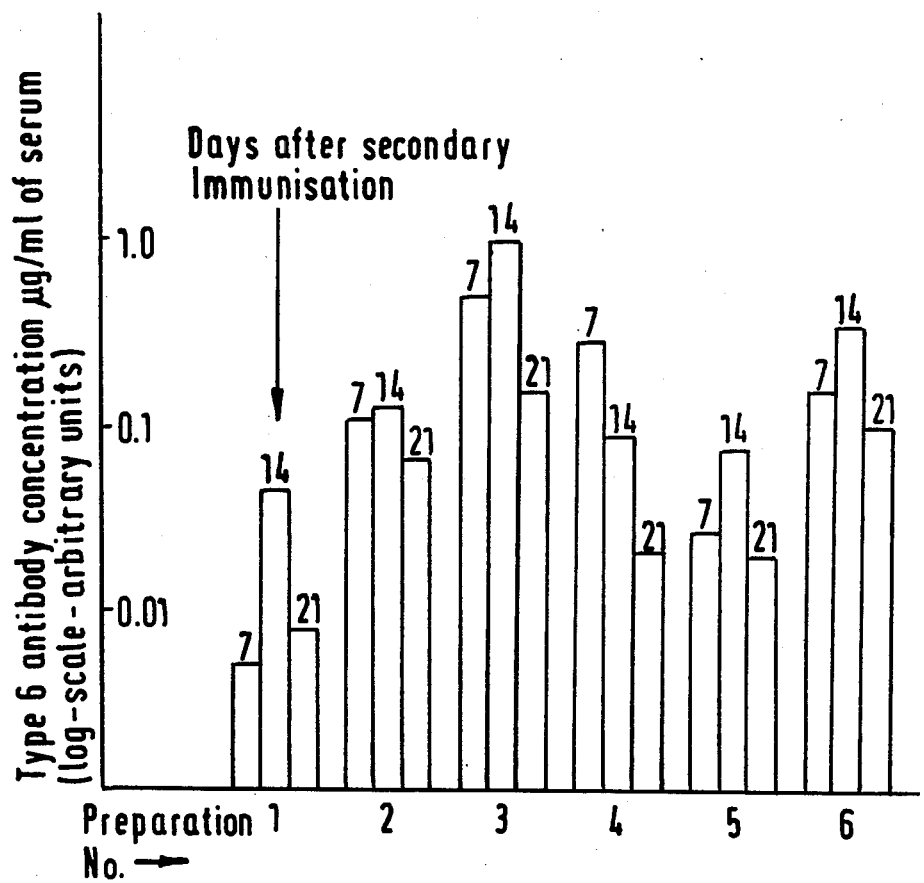
FIG. 7 shows the antibody response in mice with respect to serotype 6 antigens after secondary immunisation with B6 and aluminium-B6 preparations, and with controls.

The antibody responses to each preparation for group B and type 6 antigens are respectively shown in FIGS. 6 and 7.

EXAMPLE F

Preparation of Vaccine Formulation

The purified complexes obtained from Examples 1–6 were each dissolved as 1.0 mg per ml of aqueous sterile sodium phosphate (0.01M, pH 7.2). To the resulting solutions, was added 50 mg/ml of lactose with mixing. The solutions were then freeze-dried and stored at −20° C. until used. Reconstitution was achieved after thawing, by solution to the original volume, in sterile, pyrogen-free water.

We claim:

1. A process for the isolation of a protein-polysaccharide complex from a culture of a Gram negative bacterium, said bacterium having an outer membrane and a capsule, wherein the protein in said complex is a constituent of said outer-membrane and said polysaccharide is a constituent of said capsule, said process comprising:
   (i) producing an aqueous phase comprising a complex of said bacterial capsular polysaccharide and said bacterial outer-membrane protein by culturing, in an aqueous medium, said bacterium
   (ii) admixing the aqueous phase obtained in step (i) with an amount of a quaternary ammonium salt, effective to precipitate said complex;
   (iii) admixing the precipitate obtained in step (ii) with a water-soluble salt of calcium or magnesium in an aqueous medium to form an aqueous solution which includes said complex as a solute;
   (iv) admixing the aqueous solution obtained in step (iii) with an amount of a lower alkanol, effective to precipitate said complex, said lower alkanol being present in the resulting admixture at a concentration of from 50%–95% v/v, and
   (v) separating the complex from any other components present in the precipitate resulting from step (iv).

2. A process as claimed in claim 1 when used to prepare a complex comprising meningococcal capsular polysaccharide selected from the class consisting of those polysaccharides specific to serogroups A, B and C, and meningococcal outer-membrane protein selected from the class consisting of those proteins specific to serotypes 2, 6 and 7.

3. A process as claimed in claim 1, wherein in step (i) the aqueous phase is obtained before the culture has reached its stationary phase.

4. A process as claimed in claim 1, wherein the step (ii), the quaternary ammonium salt is cetyl-trimethylammonium bromide.

5. A process as claimed in claim 4, wherein the aqueous phase obtained in step (i) is admixed with the quaternary ammonium salt at a temperature in the range from 12° to 25° C.

6. A process as claimed in claim 5, wherein the aqueous phase obtained in step (i) is admixed with the quaternary ammonium salt at a temperature at or about 18° C.

7. A process as claimed in claim 4, wherein the cetyl-trimethylammonium bromide is present at about 1% w/v.

8. A process as claimed in claim 1, wherein in step (ii), the quaternary ammonium salt is cetylpyridinium chloride.

9. A process as claimed in claim 8, wherein the aqueous phase obtained in step (i) is admixed with the quaternary ammonium salt at a temperature in the range from 0° to 10° C.

10. A process as claim in claim 9, wherein the aqueous phase obtained in step (i) is admixed with the quaternary ammonium salt at a temperature at or about 4° C.

11. A process as claimed in claim 8, wherein the cetylpyridinium chloride is present at about 1% w/v.

12. A process as claimed in claim 1, wherein in step (iii), the water-soluble salt is calcium chloride.

13. A process as claimed in claim 1, wherein in step (iv), the alkanol is in an amount and at a concentration so that there occurs substantially no dissociation of said complex.

14. A process as claimed in claim 13, wherein the alkanol is added in sufficient amount to provide a concentration of about 75% w/v when in admixture with the aqueous solution.

15. A process as claimed in claim 1, wherein in step (iv), the alkanol contains from 1 to 4 carbon atoms.

16. A process as claimed in claim 15, wherein the alkanol is selected from ethanol or methanol.

17. A process according to claim 1 wherein the precipitate obtained in step (iv) comprises said complex and other components from said culture and comprising in step (v) separating the complex from said other components by gel filtration.

* * * * *